United States Patent
Shankar et al.

(10) Patent No.: US 7,914,767 B2
(45) Date of Patent: Mar. 29, 2011

(54) ORAL DTPA FOR RADIONUCLIDE CHELATION

(75) Inventors: Gita Natarajan Shankar, Saratoga, CA (US); Helen Jaber Parish, Sunnyvale, CA (US)

(73) Assignee: SRI International, Menlo Park, CA (US)

( * ) Notice: Subject to any disclaimer, the term of this patent is extended or adjusted under 35 U.S.C. 154(b) by 1079 days.

(21) Appl. No.: 11/705,938

(22) Filed: Feb. 14, 2007

(65) Prior Publication Data

US 2007/0196273 A1 Aug. 23, 2007

Related U.S. Application Data

(60) Provisional application No. 60/774,935, filed on Feb. 17, 2006.

(51) Int. Cl.
*A61K 51/00* (2006.01)
*A61M 36/14* (2006.01)

(52) U.S. Cl. .................................. 424/1.11; 424/1.65

(58) Field of Classification Search .................. 424/1.65
See application file for complete search history.

(56) References Cited

U.S. PATENT DOCUMENTS

| | | | | |
|---|---|---|---|---|
| 5,730,968 A * | 3/1998 | Butterfield et al. | ........ | 424/78.37 |
| 6,017,522 A | 1/2000 | Butterfield | | |
| 2004/0191169 A1 * | 9/2004 | Scheinberg et al. | ......... | 424/1.49 |
| 2008/0029625 A1 * | 2/2008 | Talton | .............................. | 241/21 |

OTHER PUBLICATIONS

Yüksel et al. (Eur. J. Pharm. Biopharm. 2003, 56, 453-459).*
Šimonović et al. (J. Appl. Toxicol. 1986, 6, 109-111).*
Conrad et al. (J. Cell Biol. 1986, 103, 439-450).*
Strickley (Pharm. Res. 2004, 21, 201-230).*
Schulze et al. (Int. J. Pharm. 2005, 300, 67-75).*
Duffield J R et al: "Computer simulation of metal ion equilibria in biofluids. IV. plutonium speciation in human blood plasma and chelation therapy using polyaminopolycarboxylic acids" Journal of Inorganic Biochemistry, Elsevier Inc, US, vol. 20, No. 3, Mar. 1, 1984, pp. 199-214.
Phan et al: "Pharmacokinetics of DTPA entrapped in conventional and longcirculating liposomes of different size for plutonium decorporation" Journal of Controlled Release, Elsevier, Amsterdam, NL, vol. 110, No. 1, Dec. 10, 2005, pp. 177-188.
Kaminski M 0 et al: "Detoxification of blood using injectable magnetic nanospheres: A conceptual technology description" Journal of Magnetism and Magnetic Materials, Elsevier Science Publishers, Amsterdam, NL, vol. 293, No. 1, May 1, 2005, pp. 398-403.
Blank M L et al: "Liposomal preparations of calcium- or zinc-DTPA have a high efficacy for removing colloidal ytterbium-169 from rat tissues" Toxicology, Limerick, IR, vol. 30, No. 4, Apr. 16, 1984, pp. 275-281.
Aungst B J: "Intestinal Permeation Enhancers" Journal of Pharmaceutical Sciences, American Pharmaceutical Association, Washington, US, vol. 89, No. 4, Apr. 1, 2000, pp. 429-442.
Bulman R A et al: "Investigations Into Techniques for Removing Intra Cellular Plutonium 2. Complexing Agents Bound to Macro Molecules" Health Physics, Lippincott, Williams & Wilkins, Hagerston, MD, USA, vol. 40, No. 2, Jan. 1, 1981, pp. 228-231.
Kargacin B. et al.: 'Reduction of strontium-85 cesium-137 iodine-131 andcerium-141 retention in rats by simultaneous oral administration of calcium alginate, ferrihexaxyanoferrate(II). KI, ZN-DTPA' Health Physics vol. 49, No. 5, 1985, pp. 859-864 (abstract).
Kostial K. et al.: 'Oral zinc-OTPA treatment reduces cadmium absorption and retention in rats' Toxicology Letters vol. 39, No. 1, 1987, pp. 71-76.
Extended European search report for 07808982.8, corresponding to US 11705938, Mar. 16, 2010.
Aschar-Sobbi et al. "High Sensitivity, Quantitative Measurements of Polyphosphate Using a New DAPI-Based Approach" J Fluorese (2008) 18:859-866.

* cited by examiner

*Primary Examiner* — Michael G Hartley
*Assistant Examiner* — Melissa Perreira
(74) *Attorney, Agent, or Firm* — Richard Aron Osman

(57) ABSTRACT

A composition for oral radionuclide chelation therapy comprises a DTPA chelate selected from Zn-DTPA and Ca-DTPA and a permeation enhancer that preferentially increases jejunal uptake of the DTPA chelate. The composition has a DTPA chelate bioavailability of at least 10% of the chelate when orally administered to a mammal.

21 Claims, No Drawings

ORAL DTPA FOR RADIONUCLIDE CHELATION

CROSS-REFERENCE TO RELATED APPLICATIONS

This application claims priority to U.S. patent application Ser. No. 60/774,935, filed Feb. 17, 2006.

Statement regarding federally sponsored research: This invention was made with government support under contract numbers N01-AI-05414 and N01-AI-50047 awarded by the National Institute Of Allergy and Infectious Diseases. The government has certain rights in this invention.

BACKGROUND OF THE INVENTION

The field of the invention is treatment of radionuclide contamination with calcium diethylenetriaminepentaacetate (Ca-DTPA) and zinc diethylenetriaminepentaacetate (Zn-DTPA).

Ca-DTPA and Zn-DTPA pentetate have been shown to be effective in treating internal contamination with radionuclides such as plutonium, americium, or curium. DTPA increases the rates of elimination of these substances from the body through the exchange of calcium or zinc ions with the transuranium element. The transuranium-DTPA complex is stable and is excreted in urine.

Formulations of Ca-DTPA and Zn-DTPA suitable for intravenous administration, or inhalation via nebulizer, were approved by the FDA in August 2004 for the elimination of known or suspected internal contamination with the transuranic metals (Z>92) plutonium, americium, and curium.

Other formulations (for example oral, inhalation or transdermal) would be more easily administered than the injectable formulations; however, because of its hydrophilicity, DTPA is poorly absorbed when administered by these routes. Oral administration of Ca-DTPA and Zn-DTPA for radionuclide chelation has been described (Kostial et al, Int. J. Radiat. Biol (1987) 52:501-504; Volfet al, Int J Radiat Biol (1999) 75:929-41); and Durbin et al., Radiat Prot Dosimetry (2003) 105:503-8.); however, formulations that increase the oral bioavailability of Ca-DTPA or Zn-DTPA have not been reported.

The National Instituted of Allergy and Infectious Diseases (NIAID) issued a solicitation (RFP-NIH-NIAID-DAIT-05-46 "Development of Improved DTPA for Radionuclide Chelation", Apr. 26, 2005) stating its interest in facilitating the discovery and demonstration of proof-of-concept of prodrugs, alternative formulations, or alternative delivery methods of DTPA that provide for plasma levels sufficient to decorporate systemic transuranic compounds for use by the general public in the case of a radiation emergency.

SUMMARY OF THE INVENTION

One aspect of the invention is a composition for oral radionuclide chelation therapy, said composition comprising: a DTPA chelate selected from Zn-DTPA and Ca-DTPA; and a permeation enhancer that preferentially increases jejunal uptake of the DTPA chelate, wherein the composition has a DTPA chelate bioavailability of at least 10% of the chelate when orally administered to a mammal.

In specific embodiments, the intestinal permeation enhancer is selected from medium-chain glycerides, macrogolglycerides, polyglycols, and mixtures thereof and comprises less than 40 wt % of the composition. In a preferred embodiment, the intestinal permeation enhancer comprises caprylocaproyl macrogol-8-glyceride. The DTPA chelate preferably comprises at least 20 wt. % of the composition. The composition may be in a unit dosage form, such as a tablet or capsule, and optionally has an enteric coating. In preferred embodiments, the DTPA chelate bioavailability is at least 20%. In a specific embodiment, the composition is in a unit dosage form comprising at least 250 mg of the DTPA chelate and the DTPA chelate bioavailability is at least 25%. The composition may further comprise a P glycoprotein (Pgp) inhibitor.

In one embodiment, the composition is in the form of extruded beads contained within a capsule. The beads may have an average diameter between 0.1-1 mm. In another embodiment, the composition is in a thixotropic form contained within a capsule.

Another aspect of the invention is a method for chelating radionuclides in a mammal, the method comprising administering to the mammal a composition comprising: a DTPA chelate selected from Zn-DTPA and Ca-DTPA; and a permeation enhancer that preferentially increases jejunal uptake of the DTPA chelate, wherein the composition has a DTPA chelate bioavailability of at least 10% of the chelate when orally administered to a mammal.

Another aspect of the invention is a kit comprising a composition comprising: a DTPA chelate selected from Zn-DTPA and Ca-DTPA; and a permeation enhancer that preferentially increases jejunal uptake of the DTPA chelate, wherein the composition has a DTPA chelate bioavailability of at least 10% of the chelate when orally administered to a mammal. In certain embodiments, the kit further comprises a Pgp inhibitor.

DETAILED DESCRIPTION OF SPECIFIC EMBODIMENTS OF THE INVENTION

The present invention provides compositions, kits, and methods for oral radionuclide chelation therapy. The composition comprises a DTPA chelate selected from diethylenetriaminepentaacetate, which has a molecular formula of $CaC_{14}H_{18}N_3O_{10}$, and zinc diethylenetriaminepentaacetate, which has a molecular formula of $ZnC_{14}H_{18}N_3O_{10}$, these compounds and pharmaceutically acceptable salts thereof are referred to herein as Ca-DTPA and Zn-DTPA, respectively. References herein to Ca/Zn-DTPA refer to Ca— and/or Zn-DTPA.

The composition further comprises a permeation enhancer that increases uptake and bioavailability of the DTPA chelate subsequent to oral administration. Enhancers that maximize DTPA chelate absorption at the jejunum are particularly preferred. Numerous intestinal permeation enhancers and their preferential sites of absorption are known (see Aungst et al, J. Pharm Sci (2000) 89:429-442). The preferential site of absorption of a permeation enhancer/drug combination can also be determined using routine methods, such as the Ussing chamber method (see e.g. Gotoh et al, J Biomol Screen. (2005) 10:517-523; and Example 1 below). Preferred enhancers are selected from medium-chain glycerides, macrogolglycerides, polyglycols, glycerol esters of fatty acids, pegylated alcoholic esters of fatty acids, glyceryl monoesters, propylene glycol monoesters and mixtures thereof. The term medium-chain glycerides (MCGs) generally refers to monoglycerides and diglycerides of fatty acid, and may contain triglycerides as well as monoglycerides and diglycerides of shorter and longer chain fatty acids. Examples of preferred MCGs include glyceryl monooleate (oleic acid acyl chain) and glyceryl monolinoleate (linoleic acid acyl chain). Examples of preferred macrogolglycerides are lauroyl macrogol-32 glycerides, sold as GELUCIRE 44/14 (Gattefosse Corporation, Paramus, N.J.) and caprylocaproyl macrogol-8 glycerides, sold as LABRASOL (Gattefosse Corporation, Paramus, N.J.).

In particular embodiments, such as for loading into capsules, the compositions are preferably thixotropic; compositions that can be easily filled into capsules as liquids, yet do not leak from the capsules upon rest. This embodiment encompasses enhancers that are thixotropic macrogolglycerides. A particularly preferred such enhancer is a mixture of d-α-tocopheryl polyethylene glycol 1000 succinate (TPGS) (Eastman Vitamin E TPGS, Eastman, Kingsport, Tenn.) with caprylocaproyl macrogol-8 glycerides. TPGS is prepared by esterifying d-alpha-tocopheryl acid succinate with polyethylene glycol 1000. Another preferred enhancer is a mixture of TPGS with polysorbates, which are derived from PEGylated sorbitan (a derivative of sorbitol) esterified with fatty acids.

The permeation enhancer in the composition is provided in an effective amount, preferably at or above but proximate to a minimal effective amount, preferably less than about 80% by weight (wt. %) of the composition. More preferably, the amount of intestinal permeation enhancer is less than 60, 50, 40 or 30 wt. %. The DTPA chelate preferably comprises at least 20% by weight of the composition. More preferably, the composition comprises at least 30, 40, 50, 60, 70, or 80 wt % of the composition. In some embodiments, the composition consists essentially of the permeation enhancer and the DTPA chelate, particularly in the case of liquid formulations (e.g. liquid filled capsules described in Example 5 below). In other embodiments, the composition comprises additional excipients, binders, etc. for example to facilitate formulation into tablets, pellets, beads (e.g. multiparticulate beads described in Example 6 below), etc.

Intestinal epithelial cells express transport systems that actively remove certain compounds from the cells, transporting them in the blood-to-lumen direction. We have found that these transport systems are operative against Ca/Zn-DTPA. Accordingly, the composition may further comprise a secretory transport inhibitor. In specific embodiments, the transport inhibitor is a Pgp inhibitor such as TPGS, quinidine, digoxin, and verapamil. Numerous other suitable Pgp inhibitors are well-known (see e.g. Aungst, supra). The Pgp inhibitor maybe administered as a predose in a liquid or solid form at a specified time interval (e.g. 5, 10, 15, 30, 60 minutes) prior to administration of the DTPA oral dose. Alternatively, the Pgp inhibitor may be co-formulated with the DTPA chelate. In one co-formulation, the Pgp inhibitor, DTPA chelate, and enhancer are combined in a homogenous mixture or solution that can be filled into capsules. In another embodiment, the Pgp inhibitor is included as a solid in a solid/liquid matrix comprising the DTPA chelate and enhancer. In yet another formulation, the DTPA chelate and enhancer are formulated in a matrix with an outer sheathing of the Pgp inhibitor present as an outside shell. The capsule with the inner core of DTPA/enhancer and the outer layer of Pgp inhibitor can then be coated by an enteric coating to promote delivery of both the inner core of drug and the outer covering of Pgp inhibitor at the target site.

In preferred embodiments, the composition is formulated in unit dosage form, such as in tablets or capsules. The dosage forms may be enteric-coated. Enteric coating formulations and methods are well-known in the art; specific formulations and methods are provided in Examples 5 and 6. Each unit dosage form typically comprises a fractional daily dose of the composition. Suitable dosages generally correspond to the dosages approved by the FDA for the Ca/Zn-DTPA intravenous formulation. For adult and adolescent humans, the daily dose is roughly 1 gm of bioavailable Ca/Zn-DTPA. For children less than 12 years of age, the daily dose is approximately 14 mg/kg/day up to 1 gm/day. As an example, a capsule that contains 275 mg Ca/Zn-DTPA formulated such that the composition has a DTPA chelate bioavailability of approximately 35%, comprises approximately 1/10th of a daily dose of the composition for an adult human. Preferably, the unit dosage form comprises at least 200, 225, 250, 275, 300, 325, 350, 375, 400, 450, or 500 mg Ca/Zn-DTPA, with the remainder of the dosage form comprising the enhancer and any additional components (e.g. excipients, Pgp inhibitor, etc.), wherein the composition has a DTPA chelate bioavailability of at least 10%, 15%, 20%, 25%, 30%, 35% or 40%.

In a preferred embodiment, the composition is formulated as extruded beads, which can be filled into capsules. In addition to the permeation enhancer and DTPA chelate, these compositions will contain thickeners, such as silica (e.g. Cabosil, Cabot Corp., Boston, Mass.) and/or polymer thickeners (e.g. Methocel, Dow Corp, Midland, Mich.). Methods of making pharmaceutical compositions in the form of extruded beads are well-known. An exemplary formulation and method are provided in Example 6. The beads typically have an average diameter between 0.1-1.5 mm, and are preferably between about 0.5-1 mm.

The compositions are formulated such that the bioavailability of the DTPA chelate when orally administered to a mammal is at least 10%, and is preferably at least 15, 20, 25, 30, or 35%. Oral bioavailability is assessed using the Beagle dog, or equivalent model, wherein levels of plasma Ca/Zn-DTPA from an orally administered composition are compared to levels obtained after i.v. administration using the calculation: $BA = AUC_{PO} \times Dose_{iv} / AUC_{iv} \times Dose_{PO}$; where BA=bioavailability and AUC=area under the plasma concentration-time curve. Bioavailability studies are detailed in Example 2 below.

The above-described composition is orally administered to a mammal that has been exposed to radionuclide contamination. In specific embodiments, the mammal is a human. In other embodiments, the mammal may be a livestock animal (horse, cow, pig, etc.) or a companion animal (e.g. dog, cat, etc.). For humans, the daily dose of absorbed Ca/Zn-DTPA for effective radionuclide chelation is roughly 1 g.

In certain embodiments, a separately formulated Pgp inhibitor is administered prior to or together with the DTPA chelate composition. The composition may be provided in a kit with instructions on proper dosing. For example, the composition may be provided in a blister-pack kit, where one or more unit dosage forms are contained in a blister. The blister packaging may contain writing adjacent a blister or a row or column of blisters to indicate the proper timing of dosing. The kit may additionally contain a separately formulated Pgp inhibitor.

EXAMPLE 1

Determining Effective Combination of Permeation Enhancers and Other Additives for Intestinal Absorption The primary objective of these in vitro studies was to determine a formulation containing permeation enhancers/other additives that achieved maximum transport of DTPA from mucosal to serosal side of the intestine. The mucosal to serosal absorption of DTPA (Zinc/Calcium) was measured in vitro across harvested rat intestinal segments and colon, in an EasyMount Ussing System (Physiological Instruments Inc., CA, Item #EM-CSYS-8). The Ussing chamber consists of two diffusion chambers, a heating block for temperature control, needle valves for gas flow adjustment and gas lift stirring, and Ag/AgCl voltage and current electrodes for measuring transepithelial voltage and for passing current. Representative sections of the harvested rat small intestinal segments (jejunum, duodenum, and ileum) and the rat colon were mounted on sliders placed between the chambers, and DTPA (Zinc/Calcium) transport across the sections was monitored. Aliquots of sample solution were removed from the 'serosal' side at 30 min intervals and analyzed by high performance liquid chromatography (HPLC). The change in mucosal to serosal transport of DTPA (Zinc/Calcium) in the presence of different permeation enhancers was determined.

Zn-DTPA and Ca-DTPA was dissolved in HEPES buffer (VWR, Brisbane, Calif.), with or without additives, at the predetermined drug concentrations. HEPES buffer was used as the base mucosal and serosal fluid. Before initiating the experiment, 5 ml of HEPES buffer was added to each of the two chambers (mucosal and serosal) and was allowed to equilibrate for 20 min. Next, the mucosal buffer was replaced by the appropriate formulation to be tested and the experiment was initiated. Aliquots (0.5 ml) were collected from the serosal side and were replaced with an equivalent amount of fresh HEPES buffer (maintained at physiological temperature). The aliquotted samples from the serosal side were analyzed by HPLC.

Owing to the expected variation in the in vitro conditions and harvested rat intestinal segments, five replicates were used per experimental condition. In order to compare data obtained from the different experiments, the apparent permeability coefficients ($P_{app}$) were calculated according to:

$$P_{app} = \frac{dQ/dt}{C_0 \times A}$$

Where, $dQ/dt$ is the linear appearance rate of mass in receiver compartment, $C_0$ is the initial solute concentration in donor compartment, and A is the surface area. $P_{app}$ values for transport for Zn-DTPA and Ca-DTPA are listed in Table 1. The higher the $P_{app}$ value, the better the permeation property. The similarity of the $P_{app}$ values indicates similar behavior for the two DTPA compounds.

TABLE 1

Transport of 5 mg/ml of DTPA in HEPES Buffer

| | Ca-DTPA | | Zn-DTPA | |
|---|---|---|---|---|
| Tissue | Papp ($\times 10^{-6}$ cm/sec) | STDEV ($\times 10^{-6}$) | Papp ($\times 10^{-6}$ cm/sec) | STDEV ($\times 10^{-6}$) |
| Duodenum | 1.71 | 0.17 | 1.65 | 0.14 |
| Jejunum | 3.84 | 0.14 | 4.54 | 0.39 |
| Ileum | 2.80 | 0.11 | 2.07 | 0.13 |
| Colon | 3.22 | 0.51 | 2.39 | 0.38 |

We then evaluated transport of Zn-DTPA and Ca-DTPA through jejunum segments with and without Labrasol. Results are in Table 2.

TABLE 2

| | | Ca-DTPA | | Zn-DTPA | |
|---|---|---|---|---|---|
| Formulation | | Papp ($\times 10^{-6}$ cm/sec) | STDEV ($\times 10^{-6}$) | Papp ($\times 10^{-6}$ cm/sec) | STDEV ($\times 10^{-6}$) |
| 5 mg/ml of drug | in HEPES Buffer | 3.84 | 0.14 | 4.28 | 0.29 |
| | in HEPES Buffer containing 10% Labrasol | 2.84 | 0.29 | NA | NA |
| | in HEPES Buffer containing 20% Labrasol | 3.48 | 0.95 | NA | NA |
| | in HEPES Buffer containing 40% Labrasol | 13.51 | 0.69 | 19.08 | 1.43 |
| 100 mg/ml of drug | in HEPES Buffer | 4.63 | 0.41 | 5.86 | 0.82 |
| | in HEPES Buffer containing 10% Labrasol | 6.29 | 0.77 | 4.21 | 0.37 |
| | in HEPES Buffer containing 20% Labrasol | 11.76 | 1.76 | 3.53 | 0.38 |
| | in HEPES Buffer containing 40% Labrasol | NA | NA | 6.81 | 0.93 |

Our data show that increased amounts of drug at constant enhancer levels increased mucosal to serosal transport of DTPA.

We then tested the transport of 100 mg/ml DTPA in HEPES buffer with and without added enhancers across jejunum segments; results are in Table 3.

TABLE 3

| | Ca-DTPA | | Zn-DTPA | |
|---|---|---|---|---|
| Formulation | $P_{app}$ ($\times 10^{-6}$ cm/sec) | STDEV ($\times 10^{-6}$) | $P_{app}$ ($\times 10^{-6}$ cm/sec) | STDEV ($\times 10^{-6}$) |
| HEPES Buffer only | 4.63 | 0.41 | 5.86 | 0.82 |
| 10% Labrasol | 6.29 | 0.77 | NA | NA |
| 20% Labrasol | 11.76 | 1.76 | NA | NA |
| 10% Tween 80 | 5.43 | 1.08 | NA | NA |
| 5% Tween 80 + 5% Labrasol | 11.61 | 2.05 | 13.27 | 2.2 |
| 10% Gelucire 44/14 | 6.57 | 0.96 | NA | NA |
| 5% Gelucire 44/14 + 5% Labrasol | 7.27 | 0.97 | NA | NA |
| 5% TPGS + 5% Labrasol | 14.04 | 4.45 | 6.34 | 0.99 |
| 5% TPGS + 20% Labrasol | 7.85 | 0.67 | NA | NA |
| 20% Bile Salt | 12.65 | 2.33 | 19.65 | 2.94 |
| 5% Tween 80 and 5% Labrafil | 2.83 | 0.35 | NA | NA |
| 5% Tween 80 and 5% Caproyl PGMC | 2.75 | 0.41 | NA | NA |
| 5% Tween 80 + 5% Capmul PG-8 | 3.61 | 0.29 | NA | NA |

Based on the values listed in Table 3, the best candidate formulations were HEPES Buffer containing 20% Labrasol, 5% Tween 80+5% Labrasol, 5% TPGS+5% Labrasol, and 20% bile salt. However, Tween 80 is used at very low concentrations (less than 1%) owing to its toxicity. Bile salts have lower approval ratings as permeation enhancers. We therefore chose to use either 20% Labrasol or 5% TPGS with 5% Labrasol for our further studies.

EXAMPLE 2

Bioavailability Study After Single Dose Administration of Radiolabeled DTPA ($^{14}$C) in Male and Female Beagle Dogs (SRI Study Nos B221-06 & B221B-06)

The objective of this study was to determine the bioavailability of radiolabeled DTPA ($^{14}$C) in male and female beagle dogs after single dose intravenous and oral administrations. Four beagle dogs were administered ~10 mg/kg Ca-DTPA, using $^{14}$C-DTPA as a tracer to quantitate exposure in plasma with time. Two dogs (1 M, 1 F) were administered the drug by the intravenous route and two other dogs (1 M, 1 F) received DTPA in an enhancer mixture filled as a liquid into in a capsule. Blood was collected and processed to plasma. Total radioactivity in the plasma was determined by liquid scintillation counting.

The pharmacokinetic parameters are provided in Table X where $C^0$ is plasma concentration at time 0, $C_{max}$ is maximum plasma concentration; AUC is area under the plasma concentration versus time curve; Cl is total clearance; $t_{1/2}$ is elimination phase half life; F is oral bioavailability.

TABLE 4

Pharmacokinetic Parameters for $^{14}$C-DTPA

| Dog | Route | $C^0$ (hr) | $C_{max}$ (ng/ml) | AUC (hr * ng/ml) | Cl (ml/hr/kg) | $t_{1/2}$ (hr) | F (%) |
|---|---|---|---|---|---|---|---|
| 1 | IV | 49.15 | | 39.65 | 252182 | 0.81[a] | |
| 2 | IV | 46.84 | | 42.89 | 233144 | 0.82[a] | |
| 3 | PO | | 0.98 | 6.96 | | 11.34 | 19.3 |
| 4 | PO | | 1.32 | 8.99 | | 11.45 | 18.0 |

[a]These parameters were determined using a two compartment model. The rest of the data were derived by noncompartmental modeling Oral bioavailability (F) for the capsule formulation evaluated in this study was 19.3% (male dog) and 18.0% (female dog). The half-life of elimination extended from 0.8 hr in the intravenous group to approximately 11 hr in the oral group.

Two additional oral formulations of Ca-DTPA were studied in male and female beagle dogs to determine the effect of modifications in the formulation on oral bioavailability (SRI Study B221B-06). The dose administered was 10 mg/kg plus ~100 µCi/kg. One male and one female dog received the drug in a bead formulation that consisted of 42.22% DTPA, 25.33% Labrasol®, 8.44% CAB-O-SIL EH5, 24.0% HPMC K110M, and 17.17% water; the other male and female dog were administered DTPA in a liquid formulation that consisted of 20% Labrasol®. In both dose groups, the formulated drug was added to size "0" capsules, then sealed and stored until administration.

Plasma drug concentrations were increased after oral administration compared to the first dog study. Table 5 summarizes the pharmacokinetic parameters determined in this study, including the oral bioavailability, which was shown to be 28.6% (male) and 38.2% (female) using the bead capsule formulation, and 30.3% (male) and 38.3% (female) with the liquid capsule formulation. The half-life of elimination was also extended in this study to about 22-27 hr in the bead capsule formulation group and 16-18 hr in the liquid capsule group.

TABLE 5

Pharmacokinetic Parameters After Oral Administration of DTPA Formulated with Labrasol ® to Beagle Dogs

| Formulation | Dog | $C_{max}$ (ng/ml) | AUC (hr * ng/ml) | $t_{1/2}$ (hr) | F (%)[a] |
|---|---|---|---|---|---|
| Granules | 1 (M) | 1.32 | 11.337 | 21.70 | 28.6 |
| | 2 (F) | 3.18 | 16.400 | 27.32 | 38.2 |
| Semisolid | 3 (M) | 2.69 | 12.006 | 16.41 | 30.3 |
| | 4 (F) | 1.62 | 16.426 | 18.27 | 38.3 |

[a]($AUC_{PO}/AUC_{IV}$) × 100

By 264 hr after dose administration, about 95-96% of the dose was recovered in the excreta (data not shown). By 24 hr, about 73-74% of the dose was excreted in the feces in both treatment groups, and this quantity is likely to represent primarily unabsorbed drug. These findings confirm that the oral bioavailability of DTPA in formulations containing Labrasol® exceeds 25%.

EXAMPLE 3

Bioavailability Study After Liquid Dose Administration of Radiolabeled DTPA ($^{14}$C) in Male Sprague-Dawley Rats (SRI Study No. B230-06)

The objective of this study was to determine the oral bioavailability of Ca-DTPA using radioactive $^{14}$C-DTPA tracer for detection in male Sprague Dawley rats after oral administration in several different formulations. The results of the study are presented in Table 6. After oral gavage of Ca-DTPA or DTPA (free acid) in sterile water, the oral bioavailability of DTPA is estimated to be about 7% in these two treatment groups. The highest area under the curve ($AUC_{oral}$) and calculated oral bioavailability was obtained in groups with 20% Labrasol, e.g. Group 4 had ~12% oral bioavailability of DTPA. In Group 7, which also was administered DTPA in 20% Labrasol (+Quinidine pretreatment), the mean bioavailability was 10%, but this group had greater interindividual variability than seen in the other treatment groups. One rat (#19) had a higher oral AUC than any others in the study, resulting in bioavailability of DTPA of 19%, indicating that quinidine was active in inhibiting efflux transport of DTPA.

Since these liquid formulations passed through the rat stomach, bioavailability readings were lower than those achieved earlier in dogs. These in-vivo data correlated well with our in vitro results

TABLE 6

AUC and Oral Bioavailability of DTPA in Sprague Dawley Rats:

| DTPA[a] | Animal # | AUC$_{0 \to last}$ (Hr * ng/ml)[b] | Mean ± SD | % Bioavailability | Mean ± SD |
|---|---|---|---|---|---|
| Group 1 IV | | | | | |
| saline | 1 | 17.34 | 17.73 ± 0.63 | 100 | 100.00 |
| Ca-DTPA | 2 | 18.4585 | | | |
| | 3 | 17.3934 | | | |
| Group 2 Oral | | | | | |
| water | 4 | 1.2411 | 1.22 ± 0.05 | 7.00 | 6.87 ± 0.27 |
| Ca-DTPA | 5 | 1.1632 | | 6.56 | |
| | 6 | 1.2516 | | 7.06 | |
| Group 3 Oral | | | | | |
| water | 7 | 1.4708 | 1.21 ± 0.29 | 8.29 | 6.80 ± 1.66 |
| free acid DTPA | 8 | 0.8897 | | 5.02 | |
| | 9 | 1.2594 | | 7.10 | |
| Group 4 Oral | | | | | |
| 20% Labrasol | 10 | 1.6901 | 2.15 ± 0.41 | 9.53 | 12.14 ± 2.29 |
| Ca-DTPA | 11 | 2.3145 | | 13.05 | |
| | 12 | 2.4507 | | 13.82 | |
| Group 5 Oral | | | | | |
| 5% Labrasol | 13 | 1.4714 | 1.26 ± 0.24 | 8.30 | 7.12 ± 1.37 |
| Ca-DTPA | 14 | 0.9971 | | 5.62 | |
| | 15 | 1.3181 | | 7.43 | |
| Group 6 Oral | | | | | |
| 5% TPGS | 16 | 1.3506 | 1.40 ± 0.15 | 7.62 | 7.909 ± 0.84 |
| +5% | 17 | 1.284 | | 7.24 | |
| Labrasol Ca-DTPA | 18 | 1.5688 | | 8.85 | |
| Group 7 Oral | | | | | |
| 0.15 mM Quin[c] | 19 | 3.3876 | 1.81 ± 1.39 | 19.10 | 10.23 ± 7.82 |
| Then | 20 | 1.2912 | | 7.28 | |
| 20% Labrasol Ca-DTPA | 21 | 0.7655 | | 4.32 | |

[a]For each group, the dose was 16.38 mg-equiv DTPA/Kg
[b]The last time point used was 3 hr for iv group and 6 hr for po groups.
[c]Quinidine was administered 20 min before formulated DTPA was administered.

EXAMPLE 4

Excretion of Iron After Repeat Dose Administration of DTPA in Male and Female Beagle Dogs (from Final Report, p. 27)

The objective of this study was to evaluate the efficacy of an oral formulation of DTPA to enhance the excretion of iron in urine from iron-loaded dogs. Iron-loaded dogs were used in the study as a surrogate model for contamination by transuranic elements.

Two treatment groups, consisting of one male and one female dog, were compared. Ca-DTPA in sterile saline was administered by the intravenous route, 10 mg/kg, on Day 1, followed by 4 days of treatment with Zn-DTPA (10 mg/kg daily). The oral treatment group was also administered 10 mg/kg in 20% Labrasol® in capsules, with Ca-DTPA on Day 1 and Zn-DTPA on Days 2-5. Blood was collected from each dog at the following time points: predose and 1, 4, 8, and 24 hr after dose administration on Day 1, and at 24 hr postdose on Days 2-5. Dogs were maintained in metabolism cages for the study, and urine was collected at 4, 8, and 24 hr after the Day 1 dose, and every 24 hr after the Day 2-5 doses. Collected samples were analyzed for iron, calcium, and zinc by Perkin-Elmer ICP (Inductively Coupled Plasma) unit.

Plasma analysis was performed for calcium (Ca), iron (Fe), and zinc (Zn). Zn was not detected in any of the plasma samples. Ca and Fe were detected but did not show any trend that appeared to be related to treatment with DTPA.

Ca levels in the urine were relatively high throughout the study and did not show a correlation with the administration of Ca-DTPA on Day 1. Excretion of Zn in the urine also did not seem to be correlated to the administration of Zn-DTPA on study Days 2-5. For both Ca and Zn, three of the four dogs (1-3), excreted similar quantities in the urine, while the fourth dog, a female in the oral treatment group, had lower total excretion of Ca and Zn. This fourth dog also excreted a lower quantity of urine, suggesting that it may not have been eating and drinking as much as the other three.

In contrast, excretion of Fe in the urine differed distinctly among the four dogs. Table 7 shows that at each urine collection time point, the excretion of Fe tended to be higher in the animals that were administered DTPA by the intravenous route. In male Dog 1 (intravenous group) and female Dog 4 (oral group), the time of highest excretion of Fe in the urine was 48 hr, while the highest excretion in the other two dogs occurred at 96 hr. Total excretion of Fe was higher in the male dogs than in the female dogs and in the animals treated by the intravenous route compared to the oral route. Nevertheless, excretion of Fe by dogs that received DTPA orally was significant, at 40% (male) and 34% (female) of the amount excreted by intravenously treated animals.

TABLE 7

Excretion of Fe in urine following DTPA administration

| | IV | | Oral | |
|---|---|---|---|---|
| Time (hr) | 1M | 2F | 3M | 4F |
| 0 | 0.1297 | 0.1158 | 0.0947 | NS[a] |
| 4 | 0.0970 | 0.0975 | 0.0654 | NS |
| 8 | 0.0471 | 0.0124 | 0.0153 | NS |
| 24 | 0.1136 | 0.0792 | 0.1000 | 0.0314 |
| 48 | 0.6044 | 0.2686 | 0.1232 | 0.1162 |
| 72 | 0.1732 | 0.1623 | 0.0506 | 0.0210 |
| 96 | 0.1762 | 0.2884 | 0.1869 | 0.0406 |
| 120 | 0.2324 | 0.0166 | 0.0506 | 0.1089 |
| Total[b] | 1.444 | 0.925 | 0.591 | 0.318 |

[a]NS = No sample
[b]Total calculated by summing the value for excretion 4 hr to 120 hr.

EXAMPLE 5

Ca/Zn-DTPA Liquid-Filled Capsule Formulation

In this formulation, the drug DTPA and Labrasol® in the amounts shown in Table 8 were uniformly mixed in a clean glass bottle with a magnetic stirrer for 15 minutes and then transferred into size "0" Licaps, hard gelatin capsules designed for liquid formulations, by means of a positive displacement pipette. The formulation was continuously stirred while 600 mg±20 mg of the formulation was manually transferred into each capsule. After the formulation was added, the capsule was stored in a Ziploc bag at room temperature until coating.

The drug-filled capsules were then base-coated using Klucel EF before the enteric coating to optimize the adhesion of enteric polymer. Hydroxy propyl cellulose (HPC), Klucel EF grade, was used as the base coating agent. An Erweka pan coater was used. A 9.0% w/w amount of Klucel EF was weighed and added to two thirds of the water, heated to >50° C., and mixed for 60 minutes using a magnetic stirrer. Then the remaining water was added, and the mixture was cooled to room temperature. This solution was prepared 24 hours prior to use. Once the coating solution was set for spraying in the pan coater, the capsules to be coated were loaded into the pan and coated according to the optimized coating parameters.

After the capsules were precoated or base coated, an optimized pan coating process was used to apply the enteric coating, Eudragit L 30D-55, an enteric polymer. For enteric coating solution, a calculated amount of Eudragit L 30D-55 was diluted with water. Then triethyl citrate and polysorbate 80, as a 33% aqueous solution, was added while the mixture was stirred with a magnetic stirrer. This dispersion was prepared 24 hr prior to use. Once the coating solution was set for spraying in the pan coater, the capsules to be coated were loaded into the pan and coated in accordance with the optimized coating parameters.

TABLE 8

Liquid-Filled Capsule Formulations

| | 14881-89 Ca-DTPA | | 14881-93 Zn-DTPA | |
|---|---|---|---|---|
| | Liquid Formulation | | | |
| Formulation | Amount (%) | Amount (g) | Amount (%) | Amount (g) |
| Ca/Zn-DTPA | 21.12 | 40.01 | 21.12 | 40.00 |
| Labrasol ® | 78.88 | 149.39 | 78.88 | 149.38 |
| Total | 100.00 | 189.40 | 100.00 | 189.38 |
| | Base Coating | | | |
| Formulation | Amount (%) | Amount (g) | Amount (%) | Amount (g) |
| Klucel EF | 9.01 | 25.00 | 9.01 | 25.01 |
| Water | 90.99 | 252.56 | 90.99 | 252.56 |
| Total | 100.00 | 277.56 | 100.00 | 277.57 |
| | Base Coating Parameters | | | |
| Pan Speed | 1 | | 1 | |
| Air Flow | 11-13 Lpm | | 11-13 Lpm | |
| Coating time | 7 hr 10 min | | 8 hr 10 min | |
| Capsule # | 105 | | 105 | |
| Weight before coating (g) | 71.96 | | 72.9 | |
| Weight after coating (g) | 76.28 | | 77.36 | |
| Weight gain/capsule (mg) | 41.14 | | 42.48 | |
| | Enteric Coating | | | |
| Formulation | Amount (%) | Amount (g) | Amount (%) | Amount (g) |
| Eudragit L30D 55 | 54.94 | 176.20 | 54.94 | 176.20 |
| Triethyl citrate | 3.30 | 10.59 | 3.30 | 10.59 |
| Tween 80 | 0.23 | 0.75 | 0.23 | 0.75 |
| Water | 41.53 | 133.19 | 41.53 | 133.19 |
| Total | 100.00 | 320.73 | 100.00 | 320.73 |
| | Enteric Coating Parameters | | | |
| Pan Speed | 2 | | 2 | |
| Air Flor | 9-10 Lpm | | 8-9 Lpm | |
| Coating time | 8 hr 40 min | | 11 hr 10 min | |
| Capsule # | 98 | | 100 | |
| Weight before coating (g) | 72.56 | | 73.97 | |
| Weight after coating (g) | 88.27 | | 86.71 | |
| Weight gain/capsule (mg) | 160.31 | | 127.40 | |

EXAMPLE 6

Ca/Zn-DTPA Multiparticulate Bead-Filled Capsule Formulation

A multiparticulate dosage form was developed in which DTPA bead formulations were prepared by using Extrusion Spheronization technology. A typical extrusion and spheronization process involves mixing the active ingredients and excipients in a mixer to be granulated. The wet granulated material is then extruded to obtain small dense pellets. The pellets are transferred into a spheronizer consisting of a rotating plate at the bottom of a chamber. The spinning movement of the pellets on the rotating plate transforms them into spheres, which are then dried. This process produces spherical and durable beads/granules.

The amounts of each component and process parameters are shown in Table 9. The process involved blending drug and CAB-O-SIL EH5. To the drug-CAB-O-SIL EH5 blend, a calculated amount of Labrasol® was added and allowed to adsorb, with mixing every 5 min for 15 min to be sure that no large agglomerates remain in the blend. HPMC K100M was then added to the drug-Labrasol® blend and mixed with a laboratory-scale planetary mixer. For the extrusion spheronization process, water was used as the binding agent. The drug excipient blend was uniformly mixed with water using a laboratory-scale planetary mixer. The blend was extruded using a Multi Granulator Model MG-55 (Extruder, LCI Corporation, NC) and then spheronized, using a Marumerizer Model QJ-230T (Spheronizer, LCI Corporation, NC), to give drug-loaded beads. These beads were dried in a hot air oven at 60° C. The beads were then sieved using a pharmaceutical sieve, and the beads that were retained on Sieve #18 were filled into /opaque white size "0" hard gelatin capsules using a semiautomatic capsule filling machine. Approximately 420 mg±20 mg of the beads were added into each capsule. The capsules were then stored coated using the procedure described in the above example.

TABLE 9

Multiparticulate Bead-Filled Capsule Formulations

| | 14881-89 Ca-DTPA | | 14881-93 Zn-DTPA | |
|---|---|---|---|---|
| Multiparticulate Bead Formulation | | | | |
| Formulation | Amt (%) | Amt (g) | Amt (%) | Amt (g) |
| Ca/Zn-DTPA | 42.22 | 126.67 | 42.21 | 105.56 |
| Labrasol ® | 25.33 | 75.98 | 25.34 | 63.38 |
| CAB-O-SIL EH 5 | 8.45 | 25.34 | 8.46 | 21.15 |
| Methocel K 100M | 24.00 | 72.01 | 23.99 | 60.01 |
| Total | 100.00 | 300.00 | 100.00 | 250.10 |
| Water (% total wt) | 19.90 | 59.70 | 14.79 | 37.00 |
| Particle size distribution by sieve analysis of extruded beads | | | | |
| Sieve # | Wt retained (g) | Amt (%) | Wt retained (g) | Amt (%) |
| 12 | 90.65 | 30.22 | 10.42 | 4.17 |
| 18 | 153.58 | 51.19 | 175.45 | 70.16 |
| 30 | 9.26 | 3.09 | 14.04 | 5.61 |
| Fines | 4.11 | 1.37 | 0.74 | 0.30 |
| Lost during process | 42.40 | 14.13 | 49.42 | 19.76 |
| Total | 300.00 | 100.00 | 250.10 | 100.00 |
| Base Coating | | | | |
| Formulation | Amount (%) | Amount (g) | Amount (%) | Amount (g) |
| Klucel EF | 9.01 | 25.00 | 9.00 | 24.99 |
| Water | 90.99 | 252.56 | 91.00 | 252.56 |
| Total | 100.00 | 277.56 | 100.00 | 277.55 |
| Base Coating Parameters | | | | |
| Pan Speed | 1 | | 1 | |
| Air Flow | 11-13 Lpm | | 11-13 Lpm | |
| Coating time | 9 hr 15 min | | 7 hr | |
| Capsule # | 250 | | 125 | |
| Weight before coating (g) | 151.18 | | 64.93 | |
| Weight after coating (g) | 155.12 | | 68.37 | |
| Weight gain/capsule (mg) | 15.76 | | 27.52 | |

TABLE 9-continued

Multiparticulate Bead-Filled Capsule Formulations

| | 14881-89 Ca-DTPA | | 14881-93 Zn-DTPA | |
|---|---|---|---|---|
| Enteric Coating | | | | |
| Formulation | Amount (%) | Amount (g) | Amount (%) | Amount (g) |
| Eudragit L30D 55 | 54.94 | 176.20 | 54.94 | 132.00 |
| Triethyl citrate | 3.30 | 10.59 | 3.30 | 7.93 |
| Tween 80 | 0.23 | 0.75 | 0.24 | 0.57 |
| Water | 41.53 | 133.19 | 41.55 | 99.89 |
| Total | 100.00 | 320.73 | 100.00 | 240.39 |
| Enteric Coating Parameters | | | | |
| Pan Speed | 2 | | 2 | |
| Air Flow | 9-10 Lpm | | 8-9 Lpm | |
| Coating time | 11 hr 5 min | | 9 hr 35 min | |
| Capsule # | 250 | | 120 | |
| Weight before coating (g) | 155.12 | | 67.08 | |
| Weight after coating (g) | 172.82 | | 78.38 | |
| Weight gain/capsule (mg) | 70.8 | | 94.17 | |

EXAMPLE 7

Accelerated Stability and Dissolution Studies

The liquid and bead formulations described in the above examples were placed in stability chambers and analyzed at specific time intervals for appearance, assay, purity, and dissolution.

Dissolution was performed in two stages: an acid stage followed by a buffer stage to closely replicate the physiological conditions encountered by the oral drug in moving from the stomach to the intestine. Dissolution was performed using standard procedures which includes using paddles as per USP conditions (Temperature: 37° C. and Paddle speed 100 RPM). A Dissolution Tester Station, 6 vessel unit (VanKel 7000), fitted with an external heater (VanKel VK750D) was used. Manual sampling was performed. A volume of 750 ml of dissolution media (0.1M Hydrochloric Acid) was added to each of the vessels. Capsules were fitted with wire-sinkers and one capsule was dropped into each of the vessels. Aliquots of 1.5 ml were removed at specific time points and analyzed by HPLC. The acid dissolution media solution was changed to a higher pH buffer composition at the end of 2 hr by adding 250 ml of 0.2 M HEPES [4-(2-hydroxyethyl)-1-piperazineethanesulfonic acid] buffer to each of the vessels. The pH was adjusted to 6.8 using 1.5 M Sodium Hydroxide. Dissolution at pH 6.8 was continued for another 6 hr. A total of eight hours of dissolution was observed for each of the formulation.

All the formulations were found to maintain their integrity in the "acid stage" dissolution phase, which lasted 2 hr. This analysis demonstrated that the enteric coatings performed well and withstood disruption of the capsule shell throughout the early 2-hr acid phase. Dissolution in the buffer stage was 100% complete for "liquid mixture formulations", but averaged about 80% complete for "bead mixture" formulations.

The "liquid filled" capsules started to stick together after 2 weeks of storage at 40° C.±2° C./75% relative humidity (RH) ±5% RH. However, this clumping together did not affect the enteric coating because these capsules did not disintegrate in the acidic phase. The "bead filled" capsules did not show any stickiness and withstood the conditions used for storage. The bead formulation proved to be most promising for commercial development. The formulations do not need refrigeration and are optimal for stockpiling.

What is claimed is:

1. A composition for oral radionuclide chelation therapy, said composition consisting of:
    a DTPA (diethylenetriaminepentaacetate) chelate selected from the group consisting of calcium-DTPA (Ca-DTPA) and zinc-DTPA (Zn-DTPA);
    a permeation enhancer that preferentially increases jejunal uptake of the DTPA chelate; and
    one or more excipients or binders to facilitate formulation;
    wherein the permeation enhancer is caprylocaproyl macrogol-8-glycerides, and the composition has a DTPA chelate bioavailability of at least 10% when orally administered to a mammal, as measured in a Beagle dog model and using the calculation: BA=AUCPO×Doseiv /AUCiv×DosePO; where BA=bioavailability, and AUC=area under plasma concentration-time curve, and said composition is (a) in an enteric-coated unit dosage form, or (b) in the form of extruded beads contained within a capsule, wherein the beads have an average diameter between 0.1-1 mm.

2. The composition of claim 1 in an enteric-coated unit dosage form.

3. The composition of claim 1 in the form of extruded beads contained within a capsule, wherein the beads have an average diameter between 0.1-1 mm.

4. The composition of claim 1 in a thixotropic form contained within a capsule.

5. The composition of claim 1 in a unit dosage form comprising 250, 275, 300, 325, 350, 375, 400, 450, or 500 mg of the DTPA chelate.

6. The composition of claim 1 wherein the excipients or binders consist of HEPES buffer.

7. A composition for oral radionuclide chelation therapy, said composition consisting of:
    a DTPA (diethylenetriaminepentaacetate) chelate selected from the group consisting of calcium-DTPA (Ca-DTPA) and zinc-DTPA (Zn-DTPA);
    a permeation enhancer that preferentially increases jejunal uptake of the DTPA chelate;
    a P glycprotein (Pgp) inhibitor; and
    one or more excipients or binders to facilitate formulation;
    wherein the permeation enhancer is caprylocaproyl macrogol-8-glycerides, the Pgp inhibitor is d-α-tocopheryl polyethylene glycol 1000 succinate, and the composition has a DTPA chelate bioavailability of at least 10% when orally administered to a mammal, as measured in a Beagle dog model and using the calculation: BA =AUCPO×Doseiv/AUCiv×DosePO; where BA =bioavailability, and AUC =area under plasma concentration-time curve, and said composition is (a) in an enteric-coated unit dosage form, or (b) in the form of extruded beads contained within a capsule, wherein the beads have an average diameter between 0.1-1 mm.

8. The composition of claim 7 in an enteric-coated unit dosage form.

9. The composition of claim 7 in the form of extruded beads contained within a capsule, wherein the beads have an average diameter between 0.1-1 mm.

10. The composition of claim 7 in a thixotropic form contained within a capsule.

11. The composition of claim 7 in a unit dosage form comprising 250, 275, 300, 325, 350, 375, 400, 450, or 500 mg of the DTPA chelate.

12. The composition of claim 1 wherein the excipients or binders consist of HEPES buffer.

13. A method for chelating radionuclides in a mammal, the method comprising:
    administering to the mammal the composition of claim 1.

14. The method of claim 13 wherein prior to the administering step, the mammal is administered a Pgp inhibitor.

15. A method for chelating radionuclides in a mammal, the method comprising:
    administering to the mammal the composition of claim 7.

16. A kit comprising the composition of claim 1, where a unit dosage form of the composition is contained in a blister.

17. A kit comprising the composition of claim 7, where a unit dosage form of the composition is contained in a blister.

18. A composition for oral radionuclide chelation therapy, said composition consisting of:
    a DTPA (diethylenetriaminepentaacetate) chelate selected from the group consisting of calcium-DTPA (Ca-DTPA) and zinc-DTPA (Zn-DTPA);
    a permeation enhancer that preferentially increases jejunal uptake of the DTPA chelate; and
    one or more excipients or binders to facilitate formulation;
    wherein the permeation enhancer is caprylocaproyl macrogol-8-glycerides, and said composition is (a) in an enteric-coated unit dosage form, or (b) in the form of extruded beads contained within a capsule, wherein the beads have an average diameter between 0.1-1 mm.

19. A composition for oral radionuclide chelation therapy, said composition consisting of:
    a DTPA (diethylenetriaminepentaacetate) chelate selected from the group consisting of calcium-DTPA (Ca-DTPA) and zinc-DTPA (Zn-DTPA);
    a permeation enhancer that preferentially increases jejunal uptake of the DTPA chelate;
    a P glycprotein (Pgp) inhibitor; and
    one or more excipients or binders to facilitate formulation;
    wherein the permeation enhancer is caprylocaproyl macrogol-8-glycerides, the Pgp inhibitor is d-α-tocopheryl polyethylene glycol 1000 succinate, and said composition is (a) in an enteric-coated unit dosage form, or (b) in the form of extruded beads contained within a capsule, wherein the beads have an average diameter between 0.1-1 mm.

20. A method for chelating radionuclides in a mammal, the method comprising:
    administering to the mammal the composition of claim 18.

21. A method for chelating radionuclides in a mammal, the method comprising:
    administering to the mammal the composition of claim 19.

* * * * *

UNITED STATES PATENT AND TRADEMARK OFFICE
CERTIFICATE OF CORRECTION

PATENT NO. : 7,914,767 B2  
APPLICATION NO. : 11/705938  
DATED : March 29, 2011  
INVENTOR(S) : Gita Natarajan Shankar et al.

Page 1 of 1

It is certified that error appears in the above-identified patent and that said Letters Patent is hereby corrected as shown below:

In The Specification

The government support paragraph at col. 1, lines 9-13 should read as follows:

This invention was made with government support under NOI-AI-05414 and NOI-AI-50047 awarded by National Institutes of Health (NIH); The government has certain rights in this invention.

Signed and Sealed this  
Twenty-sixth Day of April, 2016

Michelle K. Lee  
*Director of the United States Patent and Trademark Office*